(12) United States Patent
Richter et al.

(10) Patent No.: US 9,440,937 B2
(45) Date of Patent: Sep. 13, 2016

(54) METHOD FOR PRODUCING POLYISOCYANATES AND USE THEREOF

(71) Applicant: Bayer Intellectual Property GmbH, Monheim (DE)

(72) Inventors: Frank Richter, Leverkusen (DE); Martin Brahm, Odenthal (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/359,125

(22) PCT Filed: Nov. 27, 2012

(86) PCT No.: PCT/EP2012/073726
§ 371 (c)(1),
(2) Date: May 19, 2014

(87) PCT Pub. No.: WO2013/079481
PCT Pub. Date: Jun. 6, 2013

(65) Prior Publication Data
US 2014/0275525 A1    Sep. 18, 2014

(30) Foreign Application Priority Data
Nov. 29, 2011 (DE) .................. 10 2011 087 371

(51) Int. Cl.
| | |
|---|---|
| *C07D 273/04* | (2006.01) |
| *C07C 263/00* | (2006.01) |
| *C08G 18/16* | (2006.01) |
| *C08G 18/78* | (2006.01) |
| *C08G 18/79* | (2006.01) |
| *C08G 18/02* | (2006.01) |
| *C08G 18/09* | (2006.01) |

(52) U.S. Cl.
CPC ........... *C07D 273/04* (2013.01); *C08G 18/022* (2013.01); *C08G 18/025* (2013.01); *C08G 18/092* (2013.01); *C08G 18/095* (2013.01); *C08G 18/168* (2013.01); *C08G 18/7887* (2013.01); *C08G 18/792* (2013.01)

(58) Field of Classification Search
CPC .................. C07D 273/04; C07C 263/00
USPC ................................. 544/67; 560/355
See application file for complete search history.

(56) References Cited

U.S. PATENT DOCUMENTS

| | | | |
|---|---|---|---|
| 4,960,848 A | 10/1990 | Scholl et al. | |
| 5,013,838 A | 5/1991 | Scholl | |
| 5,914,383 A | 6/1999 | Richter et al. | |
| 6,090,939 A * | 7/2000 | Richter et al. | 544/67 |
| 6,107,484 A | 8/2000 | Richter et al. | |
| 7,030,266 B2 * | 4/2006 | Kocher et al. | 560/336 |
| 7,595,396 B2 * | 9/2009 | Richter | 544/67 |
| 2008/0161534 A1 | 7/2008 | Richter et al. | |
| 2009/0124727 A1 | 5/2009 | Nennemann et al. | |

FOREIGN PATENT DOCUMENTS

| | | |
|---|---|---|
| CA | 2244486 A1 | 2/1999 |
| EP | 0235388 A2 | 9/1987 |
| EP | 0295926 A2 | 12/1988 |
| EP | 0315692 A1 | 5/1989 |
| EP | 0339396 A1 | 11/1989 |
| EP | 0379914 A2 | 8/1990 |
| EP | 0447074 A2 | 9/1991 |
| EP | 0798299 A1 | 10/1997 |
| EP | 0896009 A1 | 2/1999 |
| EP | 0962454 A1 | 12/1999 |
| EP | 0962455 A1 | 12/1999 |
| EP | 01939171 A | 7/2008 |
| EP | 2058349 A1 | 5/2009 |

OTHER PUBLICATIONS

International Search Report for PCT/EP2012/073726 mailed Aug. 28, 2013.
Laas, H.J., et al., "The Synthesis of Aliphatic Polyisocyanates Containing Biuret, Isocyanurate or Uretdione Backbones for Use in Coatings", Journal für praktische Chemie, vol. 336, (1994), pp. 185-200.
Wendisch, D., et al., "Kernresonanzspektroskopishe Beiträge zur Struktur und Stereochemie von (cyclo)aliphatischen Isocyanaten und deren Folgeprodukten", Die Angewandte Makromolekulare Chemie, vol. 141, No. 2302, (1986), pp. 173-183.

* cited by examiner

*Primary Examiner* — Venkataraman Balasubramanian
(74) *Attorney, Agent, or Firm* — Drinker Biddle & Reath LLP

(57) ABSTRACT

The invention relates to a method for modifying isocyanates using catalysts having a water content not exceeding 1,000 ppm.

7 Claims, No Drawings

METHOD FOR PRODUCING POLYISOCYANATES AND USE THEREOF

CROSS-REFERENCE TO RELATED APPLICATIONS

This application is a national stage application (under 35 U.S.C. §371) of PCT/EP2012/073726, filed Nov. 27, 2012, which claims benefit of German Application No. 102011087371.6, filed Nov. 29, 2011, both of which are incorporated herein by reference in their entirety.

The oligo- and polymerization, here abbreviated to modification, of isocyanates has long been known. The modified polyisocyanates comprising free NCO groups, which optionally may also have been temporarily deactivated with blocking agents, are exceptionally high-quality starting materials for the preparation of a multiplicity of polyurethane plastics and coating materials.

A series of industrial methods for isocyanate modification have been established in which the isocyanate to be modified, usually a diisocyanate, is generally reacted by addition of catalysts and these are then rendered inactive (deactivated) by suitable measures, when the desired degree of conversion of the isocyanate to be modified has been reached, and the polyisocyanate obtained is generally separated from the unreacted monomer. A summary of these methods from the prior art can be found in H. J. Laas et al., *J. Prakt. Chem.* 1994, 336, 185 ff.

A particular form of isocyanate modification which leads to products having a high proportion of iminooxadiazinedione groups (asymmetric isocyanate trimers) in the method products, in addition to the long known isocyanurate structures (often up till now only referred to simply as "trimers"), is described, inter alia, in EP-A 962455, 962454, 896009, 798299, 447074, 379914, 339396, 315692, 295926 and 235388. For this purpose, (hydrogenpoly)fluorides have proven to be of value as catalysts, preferably having quaternary phosphonium cations as counterion.

A disadvantage of this method from the prior art is that the species used as catalyst partially decompose forming troublesome by-products, which manifests as a successively increasing phosphorus content in the monomer recovered (recycled material), generally, by distillation.

Although such contaminated recycled materials can be purified, cf EP-A 1939171, such a procedure is linked, however, to additional complexity which is essential to avoid.

It was an object of the invention, therefore, to provide a method for preparing polyisocyanates containing a high level of iminooxadiazinedione groups which is not afflicted by the abovementioned disadvantages: the catalysts should have an improved stability in the isocyanate medium and tend not, or in comparison with systems of the prior art, tend less to decomposition forming troublesome side components, which can accumulate in the method products, particularly the recycled material.

This is achieved by the provision of the method according to the invention.

The invention relates to the use of catalysts for preparing polyisocyanates containing iminooxadiazinedione groups by oligomerization of monomeric di- and/or triisocyanates, characterized in that the water content of the catalysts added to the isocyanates to be oligomerized does not exceed 1000 ppm.

When using catalyst mixtures, the total water content must not exceed 1000 ppm.

It cannot be inferred from the prior art documents cited above that a reduction of the water content in the catalysts of the prior art preferred for iminooxadiazinedione formation leads to a significant stabilization of this species in the isocyanate medium. EP 962 454 even explicitly mentions water as possible additive for preparing catalysts containing fluoride ions, which may be used for preparing polyisocyanates containing iminooxadiazinedione groups. Moreover, since diisocyanates are themselves reactive to water, it was rather to be expected that the "dewatering" of the catalyst occurs rapidly after contact with the isocyanate to be trimerized and therefore an upstream dewatering of the catalyst should have no influence.

The manner in which the manufacturing-dependent residual water present is removed from the catalyst (by distillation, extraction, chemical reaction with a harmless additive in the method, adsorption etc.), is irrelevant in the method according to the invention.

Therefore, the modification method according to the invention has provided an improved method for preparing polyisocyanates containing iminooxadiazinedione groups in a simple manner.

Preferred catalysts are those based on quarternary phosphonium salts having cations corresponding to the general formula $R_4P^+$, where R are the same or different, optionally branched, aliphatic, aromatic and/or araliphatic $C_1$-$C_{20}$ residues and optionally two or more substituents R may also form saturated or unsaturated rings with one another and with the phosphorus atom.

Individual phosphonium salts may be used, as well as mixtures of various phosphonium salts or mixtures of phosphonium salts with other catalysts which accelerate iminooxadiazinedione formation.

Particularly preferred catalysts are quaternary phosphonium polyfluorides of the formula $R_4P^+F^-\cdot n(HF)$, where R are the same or different, optionally branched, aliphatic, aromatic and/or araliphatic $C_1$-$C_{20}$ residues and optionally two or more substituents R may also form saturated or unsaturated rings with one another and with the phosphorus atom and n can have any values between 0.1 and 20. Individual phosphonium polyfluorides of the formula $R_4P^+F^-\cdot n(HF)$ may be used, likewise mixtures of these salts or mixtures of phosphonium polyfluorides of the formula $R_4P^+F^-\cdot n(HF)$ with other catalysts which accelerate iminooxadiazinedione formation.

The invention further provides a method for preparing polyisocyanates containing iminooxadiazinedione groups which comprises reacting
  a) at least one organic di- and/or triisocyanate,
  b) one or more catalysts having water contents not exceeding 1000 ppm in total,
  c) optionally solvent and
  d) optionally additives.

The invention further provides a method for preparing polyisocyanates containing iminooxadiazinedione groups which comprises reacting
  a) at least one organic di- and/or triisocyanate,
  b) one or more catalysts, comprising at least one phosphonium salt to be used in accordance with the invention, wherein the water contents of the catalysts do not exceed 1000 ppm in total,
  c) optionally solvent and
  d) optionally additives.

The invention further provides a method for preparing polyisocyanates containing iminooxadiazinedione groups which comprises reacting
  a) at least one organic di- and/or triisocyanate, b) one or more catalysts, comprising at least one quaternary phosphonium polyfluoride to be used in accordance with the invention, wherein the water contents of the catalysts do not exceed 1000 ppm in total, c) optionally solvent and d) optionally additives.

Here, additives are understood to mean substances which do not per se influence the water content of the catalyst, such as alcohols, stabilizers (e.g. sterically hindered phenols or amines), antioxidants etc., which are typically used in polyurethane chemistry.

The method according to the invention may be carried out in the temperature range between 0° C. and +250° C., preferably 20 to 180° C., particularly preferably 40 to 150° C. and may be interrupted at any degree of conversion, preferably after 5 to 80%, particularly preferably 10 to 60%, of the monomeric diisocyanate used have reacted.

The catalyst requirement in the method according to the invention does not differ from that observed in the bulk modification in the prior art. The catalyst may be used, for example, in a proportion between 1 mol ppm and 1 mol %, preferably between 5 mol ppm and 0.1 mol %, based on the amount of monomer.

In the method according to the invention, the catalyst may be used undiluted or dissolved in solvents. All compounds are suitable as solvents which do not react with the catalyst and are capable of dissolving the catalyst to a sufficient degree, e.g. aliphatic or aromatic hydrocarbons, alcohols, ketones, esters and ethers. Preference is given to using alcohols.

For the catalyst deactivation, a whole series of methods are in principle provided, previously described in the prior art, such as the addition of (under or over) stoichiometric amounts of acids or acid derivatives (e.g. benzoyl chloride, acidic esters of acids containing phosphorus or sulfur, these acids themselves etc., but not HF), adsorptive binding of the catalyst and subsequent removal by filtration and so on.

Following the catalyst deactivation, the unreacted monomer and optionally the accompanying solvent may be removed by means of all known separation techniques e.g. distillation, optionally in the particular embodiment of thin-layer distillation, extraction or crystallization/filtration. Combinations of two or more of these techniques may also evidently be used.

Should the polyisocyanate prepared according to the invention still contain free, unreacted monomer, e.g. the further processing to NCO-blocked products is of interest, the removal of the monomers may be dispensed with following the catalyst deactivation.

The unreacted monomer is preferably removed. The products according to the invention following the removal preferably have a residual monomer content of <0.5%, preferably <0.1% by weight.

The unreacted monomer is preferably removed by distillation.

In comparison with the catalysis, e.g. by quaternary phosphonium salts without the use of additives which remove the water from the catalyst (bulk modification, see comparative example), a distinctly improved catalyst stability is observed in the method according to the invention in otherwise identical reaction conditions which results in considerably lower phosphorus contents in the recycled material (cf. inventive examples).

The low-monomer content polyisocyanates having iminooxadiazinedione groups resulting from the method according to the invention have the same high quality level as the products which are obtained according to methods previously described in the prior art and are analytically indistinguishable from them.

According to a particular embodiment of the method according to the invention, operating in continuous mode, the oligomerization can be conducted in a tubular reactor. In this case, advantage is also taken of the lower tendency to decomposition of the catalysts according to the invention.

For carrying out the method according to the invention, all (di)isocyanates known from the prior art can in principle be used, individually or in any mixtures with each other.

Particular examples include: hexamethylene diisocyanate (HDI), 2-methylpentane-1,5-diisocyanate, 2,4,4-trimethyl-1,6-hexanediisocyanate, 2,2,4-trimethyl-1,6-hexanediisocyanate, 4-isocyanatomethyl-1,8-octanediisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI), 2,4- and 2,6-toluylene diisocyanate (TDI), bis(4-isocyanatophenyl)methane (4,4' MDI), 4-isocyanatophenyl-2-isocyanatophenylmethane (2,4'MDI) and polycyclic products which are accessible by formaldehyde-aniline polycondensation and subsequent conversion of the resulting (poly)amines to the corresponding (poly)isocyanates (polymer-MDI).

Preference is given to using: hexamethylene diisocyanate (HDI), 2-methylpentane-1,5-diisocyanate, 2,4,4-trimethyl-1,6-hexanediisocyanate, 2,2,4-trimethyl-1,6-hexanediisocyanate, 4-isocyanatomethyl-1,8-octanediisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI) and 1,3- and 1,4-bis(isocyanatomethyl)cyclohexane (H6XDI).

In this context, it is irrelevant according to which method the abovementioned (poly)isocyanates are generated, i.e. with or without using phosgene.

The products or product mixtures obtained by the method according to the invention consequently constitute multi-purpose starting materials which can be used for preparing, as required, foamed plastic(s) and paints, coating materials, adhesives and additives. They are particularly suitable for the preparation of, as appropriate, water-dispersible one- and two-component polyurethane coatings, optionally in NCO-blocked form, by reason of their reduced solution and melt viscosity in comparison to (predominantly) isocyanurate-polyisocyanate-based products at otherwise identically high or improved property profile. The method products according to the invention based on HDI, even at high dilution in coating solvents, are thus more stable towards the occurrence of flocculation and cloudiness than corresponding products based on isocyanurate.

They can be used pure or in combination with other isocyanate derivatives from the prior art, such as polyisocyanates containing uretdione, biuret, allophanate, isocyanurate and/or urethane groups whose free NCO groups optionally have been deactivated with blocking agents.

The following comparative examples and examples are intended to further illustrate the invention without, however, restricting it.

EXAMPLES

All amounts refer to the mass unless otherwise noted.

The determination of the NCO content in the resins described in the examples and comparative examples was conducted by titration according to DIN 53 185.

The phosphorus content of all samples was determined by X-ray fluorescence (XRF) analysis.

The water content of the catalyst solutions was determined by Karl-Fischer titration according to DIN 51777-2.

Mol % values were determined by NMR spectroscopy and always refer to the sum of NCO conversion products unless stated otherwise. The measurements were performed on Bruker DPX 400 or DRX 700 instruments using ca. 5% strength ($^1$H-NMR) or ca. 50% strength ($^{13}$C-NMR) samples in dry $C_6D_6$ at a frequency of 400 or 700 MHz ($^1$H-NMR) or 100 or 176 MHz ($^{13}$C-NMR) respectively. Low amounts of tetramethylsilane in the solution assigned to 0 ppm $^1$H-NMR chemical shift were employed as reference for the ppm scale. Alternatively, the $C_6D_5H$ present in the solvent was used as reference signal: 7.15 ppm $^1$H-NMR chemical shift, 128.02 ppm $^{13}$C-NMR chemical shift. Data for the chemical shift of the compounds in question were taken from the literature (cf. D. Wendisch, H. Reiff and D. Dieterich, Die Angewandte Makromolekulare Chemie 141, 1986, 173-183 and literature cited therein and EP-A 896 009.

The dynamic viscosities were determined at 23° C. using a Haake viscometer VT 550. By measurements at different shear rates, it was ensured that the flow behavior of the polyisocyanate mixtures described according to the invention and also of the comparative products corresponds to ideal Newtonian fluids. The shear rate data can therefore be omitted.

The determination of the residual monomer contents was conducted by gas chromatography.

All reactions were carried out under a nitrogen atmosphere unless otherwise stated.

The diisocyanates used are products of Bayer MaterialScience AG, D-51368 Leverkusen and all other commercially available chemicals were sourced from Aldrich, D-82018 Taufkirchen. The preparation of the hydrogen polyfluoride catalysts is described inter alia in EP-A 962454 and literature cited therein.

Example 1

Comparative Example 1000 g of HDI were charged, and freed from dissolved gases by stirring for one hour under vacuum (0.1 mbar), in a jacketed vessel with flat-ground joints which was maintained at a temperature of 60° C. by means of an external circulation and which was fitted with a stirrer, a reflux condenser connected to an inert gas unit (nitrogen/vacuum) and thermometer. After blanketing with nitrogen, 507 mg of a ca. 70% isopropanolic solution of tetrabutylphosphonium hydrogen difluoride, having a water content of 2200 ppm and 7.6% phosphorus content, were added portionwise such that the temperature of the reaction mixture did not exceed 65° C. After ca. 1 mol of NCO groups had reacted, the catalyst was deactivated by addition of an amount of p-toluenesulfonic acid (as a 40% solution in isopropanol) equivalent to the catalyst, and the mixture was then stirred for a further 30 min at the reaction temperature and subsequently processed. The workup was carried out by vacuum distillation in a thin-film evaporator of the flash evaporator (FE) type with a preevaporator (PE) connected upstream (distillation data: pressure: 0.08+/−0.04 mbar, PE temperature: 120° C., FE temp.: 140° C.), unreacted monomer being separated off as distillate and the low-monomer content polyisocyanate resin as bottom product (initial run, example 1-A). The polyisocyanate resin was separated and the distillate collected in a second stirring apparatus with flat-ground joints, identical in construction to the first, and made up to the starting amount (1000 g) with freshly degassed HDI. This was then treated again with catalyst and processed as described above. This procedure was repeated a total of five times (catalyst amounts: 456 mg; 501 mg; 490 mg; 446 mg and 458 mg). From the analysis of the phosphorus contents of the polyisocyanate resins obtained and the recycled monomer material remaining at the end of the experimental series, the phosphorus mass balance was determined. In total, it accounted for 92% recovery based on 79% of the phosphorus found in the resins and 21% in the final distillate. The mean data for the polyisocyanate resins obtained in the experiments 1-B to 1-F are as follows:

Resin yield (based on HDI used): 17.6%
NCO content 23.4%
Viscosity: 700 mPas/23° C.
Iminooxadiazinedione: 51 mol %*
Isocyanurate: 43 mol %*
Uretdione: 6 mol %*
*=based on the sum of NCO conversion products formed in the modification reaction Example 2

Inventive

The method was carried out as described in comparative example 1, with the difference that the water content of the catalyst used had been reduced to 360 ppm by prior addition to the catalyst solution of an amount of trimethyl orthoacetate equivalent to the water content.

From the analysis of the phosphorus contents of the polyisocyanate resins obtained and the recycled monomer material remaining at the end of the experimental series, the phosphorus mass balance was determined. In total, it accounted for 95% recovery based on 88% of the phosphorus found in the resins and 12% in the final distillate. The mean data for the polyisocyanate resins obtained in the experiments 2-B to 2-F are as follows:

Resin yield (based on HDI used): 18.1%
NCO content 23.5%
Viscosity: 695 mPas/23° C.
Iminooxadiazinedione: 53 mol %*
Isocyanurate: 42 mol %*
Uretdione: 5 mol %*
*=based on the sum of NCO conversion products formed in the modification reaction Example 3

Inventive

The method was carried out as described in comparative example 1, with the difference that the water content of the catalyst used had been reduced to 410 ppm by prior addition to the catalyst solution of an amount of triethyl orthoacetate equivalent to the water content.

From the analysis of the phosphorus contents of the polyisocyanate resins obtained and the recycled monomer material remaining at the end of the experimental series, the phosphorus mass balance was determined. In total, it accounted for 92% recovery based on 91% of the phosphorus found in the resins and 9% in the final distillate. The mean data for the polyisocyanate resins obtained in the experiments 3-B to 3-F are as follows:

Resin yield (based on HDI used): 18.4%

NCO content 23.5%
Viscosity: 705 mPas/23° C.
Iminooxadiazinedione: 52 mol %*
Isocyanurate: 43 mol %*
Uretdione: 5 mol %*
*=based on the sum of NCO conversion products formed in the modification reaction Example 4

Inventive

The method was carried out as described in comparative example 1, with the difference that the water content of the catalyst used had been reduced to 580 ppm by prior azeotroping with toluene and subsequent distillative removal of the toluene by successive replacement with 2-ethylhexanol. The phosphorus content of the catalyst solution was then 7.3%.

From the analysis of the phosphorus contents of the polyisocyanate resins obtained and the recycled monomer material remaining at the end of the experimental series, the phosphorus mass balance was determined. In total, it accounted for 95% recovery based on 92% of the phosphorus found in the resins and 8% in the final distillate. The mean data for the polyisocyanate resins obtained in the experiments 4-B to 4-F are as follows:

Resin yield (based on HDI used): 19.1%
NCO content 23.3%
Viscosity: 720 mPas/23° C.
Iminooxadiazinedione: 49 mol %*
Isocyanurate: 46 mol %*
Uretdione: 5 mol %*
*=based on the sum of NCO conversion products formed in the modification reaction

The invention claimed is:

1. A method for preparing polyisocyanates comprising iminooxadiazinedione groups by oligomerization of monomeric di- and/or triisocyanates comprising utilizing a catalyst, wherein the catalyst is a quaternary phosphonium polyfluoride of the formula $R_4P^+F^-.n(HF)$, where R are the same or different, optionally branched, aliphatic, aromatic and/or araliphatic $C_1$-$C_{20}$ residues and optionally two or more substituents R may also form saturated or unsaturated rings with one another and with the phosphorus atom and n can have any values between 0.1 and 20, and wherein the water content of the catalyst added to the isocyanates to be oligomerized does not exceed 1000 ppm.

2. A method for preparing polyisocyanates containing iminooxadiazinedione groups which comprises reacting
 a) at least one organic di- and/or triisocyanate,
 b) one or more catalyst, comprising at least one quaternary phosphonium polyfluoride wherein the water contents of the catalyst does not exceed 1000 ppm in total,
 c) optionally a solvent and
 d) optionally an additive.

3. The method as claimed in claim 2, wherein the method is carried out in the temperature range between 0° C. and 250° C.

4. The method as claimed in claim 2, wherein the method is interrupted after 5 to 80% of the monomeric diisocyanate used have reacted.

5. The method as claimed in claim 2, wherein the catalyst is used in a proportion between 1 mol ppm and 1 mol %, based on the amount of monomer.

6. The method as claimed in claim 2, wherein unreacted monomer is removed from the reaction mixture.

7. The method as claimed in claim 2, wherein at least one isocyanate used in the method is selected from the group consisting of hexamethylene diisocyanate (HDI), 2-methylpentane-1,5-diisocyanate, 2,4,4-trimethyl-1,6-hexanediisocyanate, 2,2,4-trimethyl-1,6-hexanediisocyanate, 4-isocyanatomethyl-1,8-octanediisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI), 2,4- and 2,6-toluylene diisocyanate (TDI), bis(4-isocyanatophenyl)methane (4,4'MDI), 4-isocyanatophenyl-2-isocyanatophenylmethane (2,4'MDI), and polycyclic products which are accessible by formaldehyde-aniline polycondensation and subsequent conversion of the resulting (poly)amines to the corresponding (poly)isocyanates (polymer-MDI).

* * * * *